(12) United States Patent
Simler

(10) Patent No.: US 6,536,431 B1
(45) Date of Patent: Mar. 25, 2003

(54) OXYGEN DISPENSER

(75) Inventor: Dominic Adam Simler, London (GB)

(73) Assignee: Oxygen Leisure Products Limited, London (GB)

( * ) Notice: Subject to any disclaimer, the term of this patent is extended or adjusted under 35 U.S.C. 154(b) by 0 days.

(21) Appl. No.: 09/505,470

(22) Filed: Feb. 16, 2000

(30) Foreign Application Priority Data

Apr. 26, 1999 (GB) ............................................... 9909514
Nov. 30, 1999 (GB) ............................................... 9928221

(51) Int. Cl.[7] ................................................. A62B 7/00
(52) U.S. Cl. ............................ 128/205.12; 128/204.18; 128/205.24; 128/205.25
(58) Field of Search ....................... 128/200.24, 202.26, 128/204.18, 204.21, 204.26, 205.11, 205.12, 205.15, 205.24, 205.25, 205.27, 205.28, 206.12, 206.15, 206.21, 206.27, 206.28, 207.14, 207.18

(56) References Cited

U.S. PATENT DOCUMENTS

| | | | | |
|---|---|---|---|---|
| 3,604,416 A | * | 9/1971 | Petrahai et al. | ........ 128/204.18 |
| 4,302,224 A | * | 11/1981 | McCombs et al. | ............ 55/160 |
| 4,345,593 A | * | 8/1982 | Sullivan | ................ 128/204.26 |
| 5,134,541 A | * | 7/1992 | Frouin | ........................ 361/334 |
| 6,208,264 B1 | * | 3/2001 | Bradney et al. | ........ 340/825.31 |
| 6,244,265 B1 | * | 6/2001 | Cronk et al. | ........... 128/200.24 |

* cited by examiner

Primary Examiner—Glenn K. Dawson
(74) Attorney, Agent, or Firm—Galgano & Burke

(57) ABSTRACT

An oxygen dispenser for dispensing substantially pure oxygen or highly oxygen enriched air. The dispenser has an oxygen concentrator or an oxygen/oxygen-enriched air-containing cylinder in fluid communicatin with a dispenser outlet via pipework, a flow control valve to control flow of oxygen or oxygen-enriched air to the dispenser outlet, the flow control valve being under the control of a controller. The dispenser unit further having a card reader for a magstripe, swipe card, smart card or similar or a receiver for credit tokens or other data credit input mechanisms whereby credit units may be input to the dispenser controller to dispense oxygen or oxygen enriched air.

29 Claims, 1 Drawing Sheet

OXYGEN DISPENSER

FIELD OF THE INVENTION

The present invention relates to an oxygen dispenser and more particularly although not necessarily exclusively to oxygen vending systems.

BACKGROUND TO THE INVENTION

The benefits of inhaling substantially pure oxygen to compensate for hypoxia are becoming increasingly broadly appreciated. Most commonly, individuals suffer from hypoxia following high levels of exertion in a relatively poorly ventilated environment. Such might be the case in a bar or night club particularly but may arise in a health club or other environment. Indeed, in cities where there is a very high level of atmospheric polution from, for example, car exhausts access to substantially pure oxygen or oxygen-enriched air may be an important factor in maintenance of good health.

Existing sources of substantially pure oxygen supply are conventionally simple oxygen cylinder based systems which have a manual valve for dispensing of the oxygen by an attendant or are adapted for self-service and have temporary storage of oxygen in a container intermediate the cylinder and mouth piece. These systems are, however, impractical for widespread usage and it is, of course, impractical to dispense individual oxygen cylinders to users.

It is a general objective of the present invention to provide an oxygen dispensing system that is versatile, being suitable for installation in any of a wide range of different environments and usable in an efficient and economic manner.

SUMMARY OF THE INVENTION

According to a first aspect of the present invention there is provided an oxygen dispenser for dispensing substantially pure oxygen or highly oxygen enriched air, which dispenser comprises a housing accommodating an oxygen concentrator in fluid communication with an air inlet of the housing and a dispenser outlet of the housing via pipework, a flow control valve to control flow of oxygen or oxygen-enriched air to the dispenser outlet, the flow control valve being under the control of a controller, the dispenser unit further having a card reader for a mag-stripe, swipe card, smart card or similar or a receiver for credit tokens or other credit data input means whereby credit units may be input to the dispenser controller to dispense oxygen or oxygen enriched air.

The valve is preferably a solenoid-operated valve and it may suitably be operated by the controller to dispense a predetermined volume of oxygen or oxygen enriched air for each unit of credit input by card or token or other means, which may include currency coins or notes.

The card is preferably a coded magnetic stripe (mag-stripe) card which may have the one or more credits on the card deleted following use.

In addition to having the automated control of the valve to dispense oxygen or oxygen enriched air in response to the credit data input by the card, tokens or other means, the unit preferably also has means operable by the user to alter flow rate and/or to switch off flow of oxygen or oxygen-enriched air. The dispenser unit suitably has a dispenser outlet to which a nasal or other dispensing cannula or dispensing mask may be fitted for each dispensing operation and which may be automatically cut off from further oxygen or oxygen-enriched air dispensing supply when the mask or cannula is detached from the dispenser outlet.

In contrast to incorporating one or more oxygen cylinders, the dispenser incorporates an oxygen concentrator, providing a substantially inexhaustible supply of oxygen-enriched air. An oxygen concentrator in its broadest sense is any device that concentrates the oxygen already present in air.

Most oxygen concentrations use PSA (Pressure Swing Adsorption) technology to concentrate the oxygen. PSA consists of a process where a gas is fed at an elevated pressure to a vessel containing an adsorbent matrix. The adsorbent matrix selectively adsorbs one or more of the non oxygen gas components such as Nitrogen and carbon dioxide. Thus, the product gas is enriched in the oxygen and any other components that have had least adsorption. The adsorbent bed is regenerated by: 1. reducing the pressure in the vessel and 2. flowing some high purity gas through the adsorbent particles. At least two adsorbent beds are used so that continuous flow of the enriched gas can be obtained. When one vessel is adsorbing gas, the adsorbent in the other vessel is being regenerated. Typical adsorbent materials which are used comprise carbon molecular sieves, zeolite molecular sleeves, activated carbon, silica gel, and activated alumina.

The oxygen dispenser is particularly efficient when the concentrator is operated continuously. This may have benefits in terms of the useable life of the oxygen concentrator or its maintenance intervals and is particularly useful in avoiding delay in supply of highly oxygen enriched air to the user. Accordingly, the dispenser is particularly preferably adapted to have the concentrator running continuously and configured to disperse the oxygen or oxygen-enriched air into the surrounding atmosphere when the flow control valve is not at its setting to direct flow of the oxygen or oxygen-enriched air to the dispenser outlet.

Suitably the solenoid valve is adapted to selectively alternate between supply to the dispenser outlet or to a venting outlet at a remote location of the dispenser housing away from the dispenser outlet.

The dispenser preferably has an exterior fan to expell air from the dispenser housing.

Preferably the venting outlet has an extractor fan to expell and disperse the oxygen or oxygen-enriched air rapidly.

Alternatively or preferably additionally, the dispenser is suitably adapted so that the oxygen or oxygen-enriched air is re-combined with the oxygen-depleted air from the oxygen concentrator as it is expelled from, or preferably prior to being expelled from, the dispenser housing. Such measures prevent any risk whatsoever of accumulation of oxygen within or in the vicinity of the dispenser other than the harmless small volumes held in the concentrator and associated pipework. There is, therefore no fire hazard and, indeed, the system is far safer than the existing systems that rely on use of pressurised oxygen cylinders.

By way of further improvement, the dispenser housing suitably has an air filtration element covering the air inlet to the housing and which is externally accessible to enable easy replacement. This will facilitate maintenance of the apparatus, reducing the need for internal servicing and is particularly valuable for environments with high levels of atmospheric polution.

For user comfort and to extend the benefits of use of the apparatus it is preferably adapted to introduce fragrance into the oxygen or oxygen-enriched air that it dispenses. Aromatherapy oils of other sources of fragrance may conveniently be introduced by coupling a vessel, such as, for example, a tube/cartridge, containing a selected oil or other source of fragrance into the air line of the nasal cannula or mask that is coupled, in use, to the dispenser outlet.

In an alternative embodiment, the apparatus may be adapted to introduce fragrance into the airline upstream of the dispenser outlet within the housing. To this end, one or more fragrance holding vessels may be coupled to the pipework leading to the dispenser outlet from the oxygen concentrator and where there are several such vessels with different fragrances there is suitably a means of switching between them. This arrangement may be particularly suitable where the apparatus is to be used in a domestic or other environment where the facility for rapid change over between a wide range of different fragrances is not of such great importance.

Turning to a second aspect of the present invention there is provided an oxygen dispenser for dispensing substantially pure oxygen or highly oxygen-enriched air, which dispenser comprises a housing accommodating an oxygen concentrator in fluid communication with an air inlet of the housing and a dispenser outlet of the housing via pipework, a flow control valve to control flow of oxygen or oxygen-enriched air to the dispenser outlet, the flow control being under the control of a controller and wherein the valve is a solenoid-operated valve which is operated by the controller to dispense a volume of oxygen or oxygen enriched air in response to activation of a switch means. The switch means may be a manually operated electrical switch or may be an electrical switch that is automatically activated by coupling a dispensing cannular or dispensing mask or the like to the dispenser outlet and suitably deactivated by uncoupling of the dispensing cannular mask or the like from the outlet.

The volume of oxygen dispensed is suitably a predetermined volume and may be controlled by dispensing at a known rate (which may be fixed at the outset or variable but monitored) for a controlled period of time. The controller accordingly preferably has a timer for timing the duration of a dispensing session.

Preferably the oxygen dispenser of the invention further comprises one or more flow sensors to sense the rate of dispensing flow of oxygen or oxygen enriched air and being operatively linked to the controller.

Preferably the oxygen dispenser of the invention further comprises one or more oxygen level sensors to sense the level of oxygen or oxygen enriched air being dispensed by the dispenser and/or the level of oxygen in the air being drawn into the oxygen concentrator, the oxygen level sensor(s) being operatively linked to the controller.

Suitably each oxygen level sensor forms part of a negative feedback loop with the controller. The signals from the oxygen level sensor(s) may be processed by the controller to dictate opening and or closure of the control valve to facilitate achievement and/or maintenance of a desired level of oxygen.

BRIEF DESCRIPTION OF THE DRAWINGS

A preferred embodiment of the present invention will now be more particularly described, by way of example, with reference to the accompanying drawings, wherein.

DESCRIPTION OF THE PREFERRED EMBODIMENT

Figure 1:
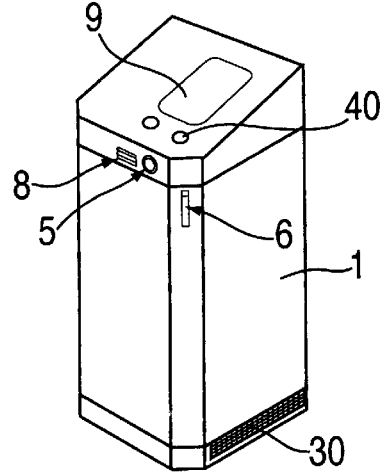
FIGS. 1 to 4 are, respectively, a perspective view, a front elevation view, a rear elevation view and a side part sectional view of an oxygen dispenser embodying the invention.
Figure 2:
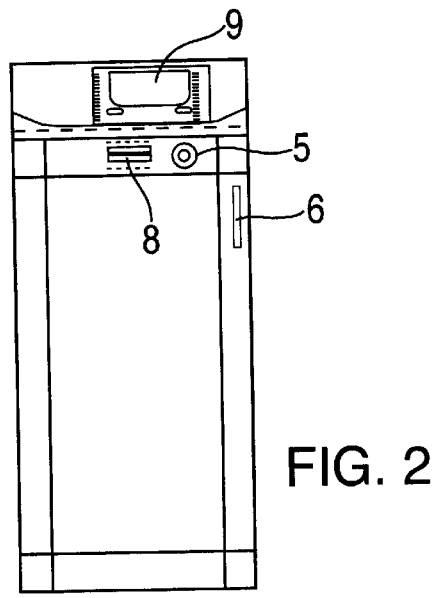
Figure 3:
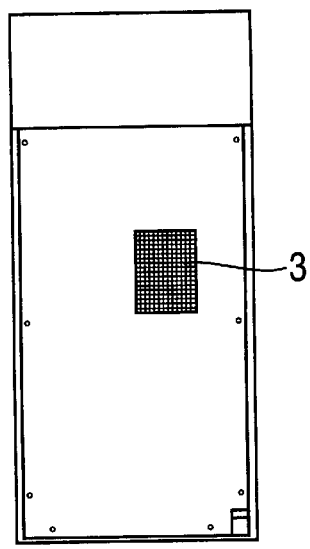

Referring to the Figures, the oxygen dispenser comprises a floor standing steel cabinet 1 housing an oxygen concentrator module 2 which is positioned within the cabinet 1 with its air inlet 50 exposed to receive air flow from a corresponding air inlet 3, in the cabinet 1. In use the oxygen concentrator is preferably powered to operate substantially continuously.

The oxygen enriched air outlet 5 of the oxygen concentrator 2 has delivery pipework 4 coupled to it and extending upwardly towards a dispensing outlet 5 of the dispenser unit.

Part way along the length of the pipework 4 is a solenoid-operated-valve 21 that is adapted to open or close the pipework 4 to permit or stop flow of the oxygen enriched air to the dispenser outlet 5. When the solenoid-operated valve 21 stops flow to the dispenser outlet 5 it instead diverts it via a discharge pipe 60 to an outlet vent 30 that vents to atmosphere. The expulsion of the oxygen enriched air is assisted by an extractor fan 31 at or near the outlet vent 30. This fan also expels the de-oxygenated air discharged from the concentrator 2 along with the oxygen enriched air preventing pressure build up within the housing 1, assisting operation of the concentrator 2 and preventing oxygen accumulation in the housing 1. Ducting may be provided extending from the deoxygenated air outlet of the compressor 2 to near the extractor fan at the housing outlet vent 30 if necessary to prevent return of the deoxygenated air to the inlet 50 of the compressor and disruption of intake of fresh air. Alternatively or additionally, and as illustrated, the air inlet 50 of the compressor may be in exclusive fluid communication with the air inlet 3 of the housing 1 via an intake duct 49.

Further along the pipe 4 before the dispenser outlet 5 the pipework 4 enters a flow meter section 6 that is externally manually adjustable by the user to control the rate of flow of oxygen-enriched air during use.

The dispenser outlet 5 comprises a socket to which a nasal cannula or tube leading to an oxygen mask is detachably coupled, in use.

This dispenser outlet 5 is adapted to automatically cut off flow of the oxygen enriched air when the cannula/oxygen mask tube is detached from the dispenser outlet 5.

Delivery of oxygen enriched air from the oxygen concentrator 2 to the dispenser outlet 5 is initiated by setting of the solenoid valve 21 to its dispensing position by a control signal from an electronic controller 7 when the electronic controller 7 of the unit registers that one or more appropriate credits have been entered into the dispenser by the user. This is suitably done by inserting a swipe or mag-stripe card into a card reader 8 in the user interface at the upper front of the cabinet. Credit data may also be input by cursor keys, a numeric or alphanumeric keypad 20. Such data may involve a unique user code. A small video display 9 confirms to the user that he has properly supplied the required credit(s) and may indicate how many credits he has remaining and/or the remaining volume or duration of oxygen-enriched air supply that he may receive.

The controller 7 comprises, in the preferred embodiment, a microprocessor linked to sensors. The controller 7 having confirmed that there is a supply of oxygen at a suitable pressure will select an appropriate dispenser outlet 5 if there are several, flash an adjacent indicator, and on confirmation by the user that he has connected himself to the system and is ready, by the user, for example, pressing a "START"

button 40 that is linked to the controller 7, the controller 7 will then send a control signal to the solenoid vale 21 to set it to deliver a flow of oxygen, for example at four liters/ minute via the solenoid-operated valve 21 for a predetermined time period or as required by the user.

For medical purposes, the swipe card may be encoded with data or signals that correspond to the medical requirements of the individual. This may restrict the duration or rate of supply of oxygen enriched air or possibly enhance it. The card may be of so-called smart card type and capable of logging details such as the parameters of each session of use of the dispenser so that the use and more particularly the nature of the use may be monitored over time. The dispenser cabinet 1 may also be adapted to enable downloading of information from the dispenser to an external computer to enable monitoring of use of the system for any of a wide variety of reasons. To this end a serial dataport or the like is suitably provided at the rear of the cabinet 1.

The normal rate of delivery of oxygen or oxygen enriched air is generally four liters per minute and suitably for a duration of a few minutes. The user may manually adjust flow via the flow meter 6 or the flow may be adjusted for him/her automatically in accordance with any details preprogrammed onto his/her card that is inserted in the card reader 8.

Figure 5:
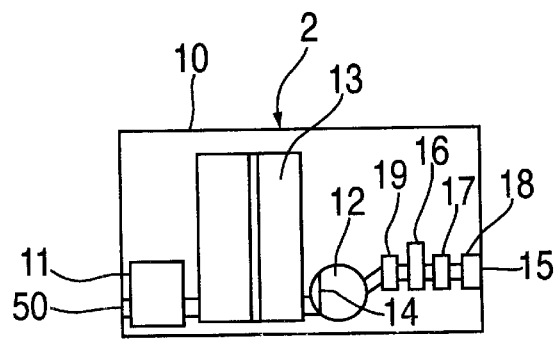
FIG. 5 is a schematic diagram illustrating components of a conventional oxygen concentrator.

With reference to FIG. 5, the oxygen concentrator module comprises an inner casing 10 within which is housed a compressor 11 to draw in air through the housing air inlet 3 and through intake duct 49 to compressor module air inlet 50 and supply it to an oxygen accumulator 12 via sleeve beds 13 and filters 14 for particulates. The oxygen enriched air or substantially pure oxygen in the accumulator is then delivered to an outlet 15 of the concentrator 2 via a bacterial filter 16, flow meter 17 and check valve 18. A pressure regulator 19 at the oxygen accumulator 12 maintains the gas within the appropriate pressure levels.

These components of the concentrator 2 may be assembled within the cabinet 1 without use of a separate inner casing 10.

For ease of maintenance the housing air inlet 3 suitably has a mesh grille that accommodates behind it a pad of filter foam to trap airborne particulates, the pad being easily externally accessible upon moving the grille to enable the filter foam pad to be cleaned and replaced or substituted with a fresh filter foam pad.

For multiple users of the oxygen dispenser it may be desirable to use, for example, twin concentrators 2 of 5 liters per minute maximum output to serve two or three dispenser outlets in a single dispenser unit 1. The maximum delivery rate may of course, be substantially greater than 5 liters (eg 10 or more liters per minute), subject to the limitations of the concentrator 2 that is used and the desired energy economy of the system.

Preferably the oxygen dispenser of the invention further comprises one or more flow sensors 70 to sense the rate of dispensing flow of oxygen or oxygen enriched air and being operatively linked to the controller. If suitably also has one or more oxygen level sensors 80*a*, 80*b*, to sense the level of oxygen in the oxygen or oxygen enriched air being dispensed by the dispenser and/or the level of oxygen in the air being drawn into the oxygen concentrator, the oxygen level sensor(s) being operatively linked to the controller.

Figure 4:
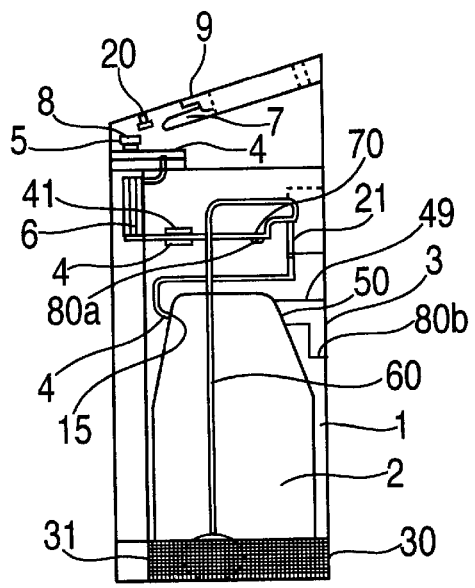

A further refinement to the system figuratively illustrated in FIG. 4 is the incorporation of delivery of fragrance chemical into the supply of oxygen or oxygen enriched air to add the benefits of aromatherapy to the existing benefits of the invention.

In the illustrated embodiment the fragrance chemicals are held in a vessel or group of vessels 41. The vessel 41, or one of the vessels 41 is, at least, in use, coupled to the pipework 4 leading from the oxygen concentrator outlet 15 to the dispenser outlet 5 and within the cabinet 1. If there are several vessels 41 these suitably each contain a different fragrance chemical and may be manually or automatically switched between.

Figure 6:
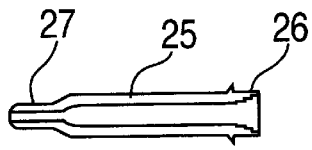
FIG. 6 is a drawing of a fragrance-containing adaptor.

An alternative arrangement for fragrance delivery involves coupling a short tubular adaptor section 25 as illustrated in FIG. 6 into the airline tubing of the mask or nasal cannula extending from the dispenser outlet 5, external to the cabinet 1, the fragrance chemical being coated on the interior of the tubular section and hence exposed to the stream of oxygen enriched air. A range of interchangeable adaptor sections each containing a different aroma may be provided. Each tubular adaptor section 25 push fits or screw fits at each end to couple to the outlet 5 at one end 26 and to the mask or nasal cannula at the other end 27.

What is claimed is:

1. An oxygen dispenser for dispensing substantially pure oxygen or highly oxygen enriched air, which dispenser comprises a housing accommodating an oxygen concentrator in fluid communication with an air inlet of the housing and a dispenser outlet of the housing via pipework, a flow control valve to control flow of oxygen-enriched air to the dispenser outlet, the flow control valve being under the control of a controller, the dispenser being adapted to have the concentrator running continuously and configured to disperse the oxygen or oxygen-enriched air into the surrounding atmosphere when the flow control valve is not at its setting to direct flow of oxygen or oxygen-enriched air to the dispenser outlet, said dispenser further having credit data input means whereby credit units may be inputted to the dispenser controller to dispense oxygen enriched air.

2. An oxygen dispenser as claimed in claim 1, wherein the valve is a solenoid-operated valve.

3. An oxygen dispenser as claimed in claim 1 wherein the valve may be operated by the controller to dispense a predetermined volume of oxygen or oxygen enriched air for each unit of credit input.

4. An oxygen dispenser as claimed in claim 1, wherein the dispenser has a card reader for a coded magnetic card.

5. An oxygen dispenser as claimed in claim 4, wherein the dispenser deletes one or more credits on the card following use.

6. An oxygen dispenser as claimed in claim 1, wherein the dispenser has means operable by the user to alter rate of flow and/or to switch off flow of oxygen or oxygen-enriched air.

7. An oxygen dispenser as claimed in claim 1 wherein the dispenser outlet is adapted to be fitted with a nasal or other dispensing cannula or dispensing mask for each dispensing operation.

8. An oxygen dispenser as claimed in claim 7 wherein the dispenser outlet is automatically cut off from further oxygen or oxygen-enriched air dispensing supply when the mask or cannula is detached from the dispenser outlet.

9. An oxygen dispenser as claimed in claim 1 wherein said flow control valve is a solenoid-operated valve which is adapted to selectively alternate between supply to the dispenser outlet or to a venting outlet at a remote location of the dispenser housing away from the dispenser outlet.

10. An oxygen dispenser as claimed in claim 9, wherein the venting outlet has an extractor fan to expel and disperse the oxygen or oxygen-enriched air rapidly.

11. An oxygen dispenser as claimed in claim 9 wherein the venting outlet has an extractor fan to expel and disperse the oxygen or oxygen-enriched air rapidly.

12. An oxygen dispenser as claimed in claim 1 wherein the dispenser has an extractor fan to expell air from the dispenser housing.

13. An oxygen dispenser as claimed in claim 1 wherein the dispenser is adapted so that the oxygen or oxygen-enriched air is re-combined with oxygen-depleted air from the oxygen concentrator as it is expelled from, or prior to being expelled from, the dispenser housing.

14. An oxygen dispenser as claimed in claim 1 wherein the dispenser housing has an air filtration element covering the air inlet to the housing and which is externally accessible to enable easy replacement.

15. An oxygen dispenser as claimed in claim 1 wherein it is adapted, in use, to introduce fragrance into the oxygen or oxygen-enriched air that it dispenses.

16. An oxygen dispenser as claimed in claim 15, wherein a fragrance holding vessel is provided which couples externally to the dispenser outlet or internally to the pipework leading to the dispenser outlet, in use.

17. An oxygen dispenser as claimed in claim 16, wherein there are a plurality of fragrance holding vessels, each vessel holding a respective fragrance, and wherein there is further provided means of switching between the vessels.

18. An oxygen dispenser as claimed in claim 16, wherein said fragrance holding vessel detachably couples in use to the dispenser outlet.

19. An oxygen dispenser as claimed in claim 1 wherein the valve is operated by the controller to dispense a volume of oxygen or oxygen enriched air in response to activation of a switch means in, or operatively associated with, the controller.

20. An oxygen dispenser as claimed in claim 19, wherein the volume of oxygen dispensed is a predetermined volume and is controlled by dispensing at a known rate for a controlled period of time, the controller further having a timer for timing the period.

21. An oxygen dispenser as claimed in claim 19 wherein said flow control valve is a solenoid-operated valve which is adapted to selectively alternate between supply to the dispenser outlet or to a venting outlet at a remote location of the dispenser housing away from the dispenser outlet.

22. An oxygen dispenser as claimed in claim 21, wherein the venting outlet has an extractor fan to expell and disperse the oxygen or oxygen-enriched air rapidly.

23. An oxygen dispenser as claimed in claim 21, wherein the venting outlet has an extractor fan to expel and disperse the oxygen or oxygen-enriched air rapidly.

24. An oxygen dispenser as claimed in claim 19 which further comprises at least one flow sensor to sense the rate of dispensing flow of oxygen or oxygen enriched air and being operatively linked to the controller.

25. An oxygen dispenser as claimed in claim 19 which further comprises at least one oxygen level sensor to sense the level of oxygen in the oxygen or oxygen enriched air being dispensed by the dispenser and/or the level of oxygen in the air being drawn into the oxygen concentrator, the oxygen level sensor being operatively linked to the controller.

26. An oxygen dispenser as claimed in claim 25 wherein said oxygen level sensor forms part of a negative feedback loop with the controller.

27. An oxygen dispenser as claimed in claim 1, wherein said credit date input means comprises a card reader.

28. An oxygen dispenser as claimed in claim 1, wherein said credit data input means comprises a receiver for credit tokens, currency coins or notes.

29. An oxygen dispenser for dispensing substantially pure oxygen or highly oxygen enriched air, which dispenser comprises a housing accommodating an oxygen concentrator in fluid communication with an air inlet of the housing and a dispenser outlet of the housing via pipework, a flow control valve to control flow of oxygen or oxygen-enriched air to the dispenser outlet, the flow control valve being under the control of a controller, the dispenser further having credit data input means whereby credit units may be input to the dispenser controller to dispense oxygen or oxygen enriched air, and wherein the dispenser is adapted so that the oxygen or oxygen-enriched air is re-combined with oxygen-depleted air from the oxygen concentrator as it is expelled from, or prior to being expelled from, the dispenser housing.

* * * * *